United States Patent [19]

De Satnick et al.

[11] Patent Number: 4,848,338

[45] Date of Patent: Jul. 18, 1989

[54] HYDRAULICALLY OPERATED SURGICAL INSTRUMENT

[75] Inventors: Allen H. De Satnick, Marblehead; Herbert D. Marcus, Winchester; Shekhar D. Nimkar, Lynn, all of Mass.

[73] Assignee: Minnesota Mining and Manufacturing Company, St. Paul, Minn.

[21] Appl. No.: 220,950

[22] Filed: Jun. 20, 1988

Related U.S. Application Data

[63] Continuation of Ser. No. 4,910, Jan. 20, 1987, abandoned.

[51] Int. Cl.⁴ .......................................... A61B 17/00
[52] U.S. Cl. ................................. 128/303 R; 128/321; 128/346; 128/312; 81/57.19; 81/57.44
[58] Field of Search ............... 128/305, 346, 326, 325, 128/318, 321, 322, 312, 303 R; 604/92; 92/60; 81/57.19, 57.44

[56] References Cited

U.S. PATENT DOCUMENTS

| | | | |
|---|---|---|---|
| 491,222 | 2/1893 | Pellet . | |
| 792,736 | 7/1905 | Sjastram . | |
| 1,271,365 | 7/1918 | Reynolds, Jr. . | |
| 1,941,593 | 1/1934 | Bellocq | 92/60 X |
| 2,082,263 | 3/1935 | Schleimer | 128/355 |
| 2,096,574 | 10/1937 | Denny | 60/52 |
| 2,113,962 | 8/1935 | Moir . | |
| 2,407,013 | 9/1946 | Field | 92/60 X |
| 2,706,922 | 4/1954 | Allen | 81/85 |
| 2,751,908 | 3/1953 | Wallace | 128/321 |
| 2,943,524 | 7/1960 | Bourne | 81/129 |
| 2,948,174 | 8/1960 | Bourne | 81/129 |
| 3,106,896 | 10/1963 | Van Der Lely et al. | 92/60 X |
| 3,298,259 | 1/1967 | Hoskin | 81/129 |
| 3,477,429 | 11/1969 | Sampson | 128/92 |
| 3,638,652 | 2/1972 | Kelley | 128/305 |
| 3,648,570 | 3/1972 | Koch | 92/60 |
| 3,752,161 | 8/1973 | Bent | 128/312 |
| 3,828,791 | 8/1974 | Santos | 128/321 |
| 4,088,134 | 5/1978 | Mazzariello | 128/321 |
| 4,201,213 | 5/1980 | Townsend | 128/312 |
| 4,258,716 | 3/1981 | Sutherland | 128/321 X |
| 4,440,170 | 4/1984 | Golden et al. | 128/325 |
| 4,501,266 | 2/1985 | McDaniel | 128/69 |
| 4,674,501 | 6/1987 | Greenberg | 128/305 |

FOREIGN PATENT DOCUMENTS

2547185 4/1977 Fed. Rep. of Germany ... 128/303 R
382369 11/1964 Switzerland ........................ 128/346

OTHER PUBLICATIONS

News Release 10/11/66–Zimmer, Warsaw, Indiana 5 Pages of Sales Brochure Published by Acufex Microsurgical, Inc. (bearing a 1981 copyright).

Primary Examiner—Michael H. Thaler
Attorney, Agent, or Firm—Donald M. Sell; Walter N. Kirn; Stephen W. Bauer

[57] ABSTRACT

A hydraulically operated surgical instrument comprising a jaw assembly including a hollow tubular outer elongate member with a first jaw member fixed to and generally radially projecting from its first end; and an inner elongated member within and extending from the first end of the outer elongate member and having a second jaw member fixed to and generally radially projecting from its end adjacent the first jaw member. The jaw assembly is mounted on a frame of the instrument with the first and second jaw members in opposed relationship and can be manually rotated about its axis relative to the frame and releasably locked in a desired position. Manual squeezing of a trigger causes movement of the jaw members between open and closed positions through a hydraulic system which limits the maximum pressure that can be applied between the jaw members.

10 Claims, 2 Drawing Sheets

HYDRAULICALLY OPERATED SURGICAL INSTRUMENT

This is a continuation of application Ser. No. 004,910 filed Jan. 20, 1987 now abandoned.

TECHNICAL FIELD

The present invention relates to fluid activated surgical instruments, and particularly to such instruments used in arthroscopic surgery.

BACKGROUND ART

Various surgical instruments have been developed, particularly for use in arthroscopic surgery, which include a jaw assembly including two elongate members each having opposed jaw members fixed to and projecting generally radially in opposed relationship from adjacent ends; and include manually actuatable means for moving the elongate members relative to each other between an open position with the jaw members spaced from each other, and a closed position with the jaw members closely adjacent each other, such as the instrument described in U.S. Pat. No. 3,752,161.

Known instruments of this type have several disadvantages when used, including a fixed relationship between the direction the jaw members project from the elongate members and a hand grip on the frame of the instrument by which the instrument is handled, which can make the instrument inconvenient to use in certain circumstances; and mechanical or high pressure gas assisted operating mechanisms which respectively limit the smoothness of operation of the operating mechanism or limit the portability of the instrument.

DISCLOSURE OF INVENTION

The present invention provides a surgical instrument of the type described above that is particularly useful for arthroscopic surgery which allows the jaw members to project in any direction with respect to the frame of the device on which the instrument is grasped, provides both smoothness of operation and portability during use, and can limit the force that can be applied between the jaw members.

According to the present invention there is provided a hydraulically operated surgical instrument comprising a jaw assembly including an outer hollow tubular elongate member having a central axis and a first jaw member fixed to and generally radially projecting from a first end of the outer elongate member; and an inner elongate member within and extending from the first end of the outer elongate member and having a second jaw member fixed to and generally radially projecting from its end adjacent the first jaw member; means for mounting the jaw assembly on a frame of the instrument with the first and second jaw members in opposed relationship while affording manual rotation of the jaw assembly about the axis of the outer elongate member relative to the frame; and manually actuatable hydraulic means for moving the outer and inner elongate members relative to each other between an open position with the jaw members spaced from each other, and a closed position with the jaw members closely adjacent each other.

Preferably the means for mounting the jaw assembly on the frame with its first and second jaw members in opposed relationship while affording manual rotation of the jaw assembly relative to the frame about the axis of the outer elongate member comprises the fame having a socket with portions of the outer and inner elongate members adjacent a second end of the outer elongate member located within the socket; bearing means between the portion of the outer elongate member in the socket and the frame for affording rotation of the jaw assembly about said axis relative to the frame; a wheel about the portion of the outer elongate member in the socket, the wheel having a periphery having portions projecting beyond the outer surface of the frame; and a pin having its ends fixed in the wheel and having a central portion extending radially through and fixed to the inner elongate member; the hollow tubular outer elongate member having axially extending slots through which the pin extends affording axial movement of the outer elongate member relative to the inner elongate member between its open and closed positions, and the slots being defined by side walls in engagement with the pin so that the outer elongate member will be rotated with the inner elongate member upon manual rotation of the wheel relative to the frame.

Also, preferably, in the hydraulically operated surgical instrument according to the present invention the manually actuatable hydraulic means for moving the outer and inner elongate members includes manually actuatable means for preventing movement of the jaw members from their closed position toward their open position which includes one way valve means for affording actuation of the manually actuatable hydraulic means to move the jaw members from their open position toward their closed position when said means for preventing movement is actuated; the manually actuatable hydraulic means for moving the outer and inner elongate members includes means for limiting the force that can be applied between the jaw members when the jaw members are moved toward their closed position; and manually actuatable means are provided for releasably locking the wheel against rotation at a predetermined position relative to the frame.

BRIEF DESCRIPTION OF DRAWING

The present invention will be further described with reference to the accompanying drawing wherein like numbers refer to like parts in the several views, and wherein.

DETAILED DESCRIPTION OF THE PREFERRED EMBODIMENT

Figures 1, 3:
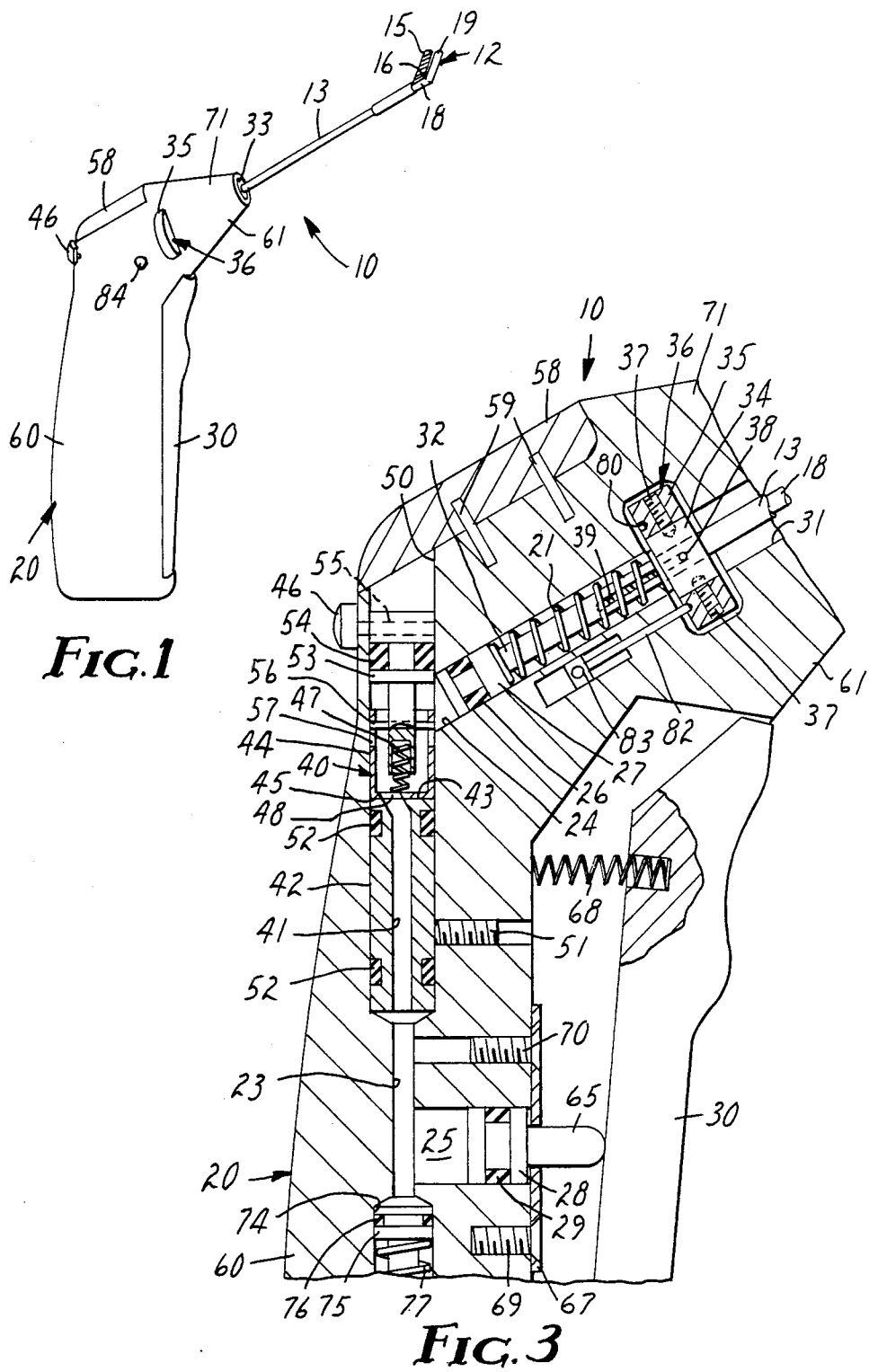
FIG. 1 is a perspective view of a hydraulically operated instrument according to the present invention.
FIG. 3 is an enlarged fragmentary sectional view of the instrument of FIG. 1 having parts broken away to show details.
Figure 2:
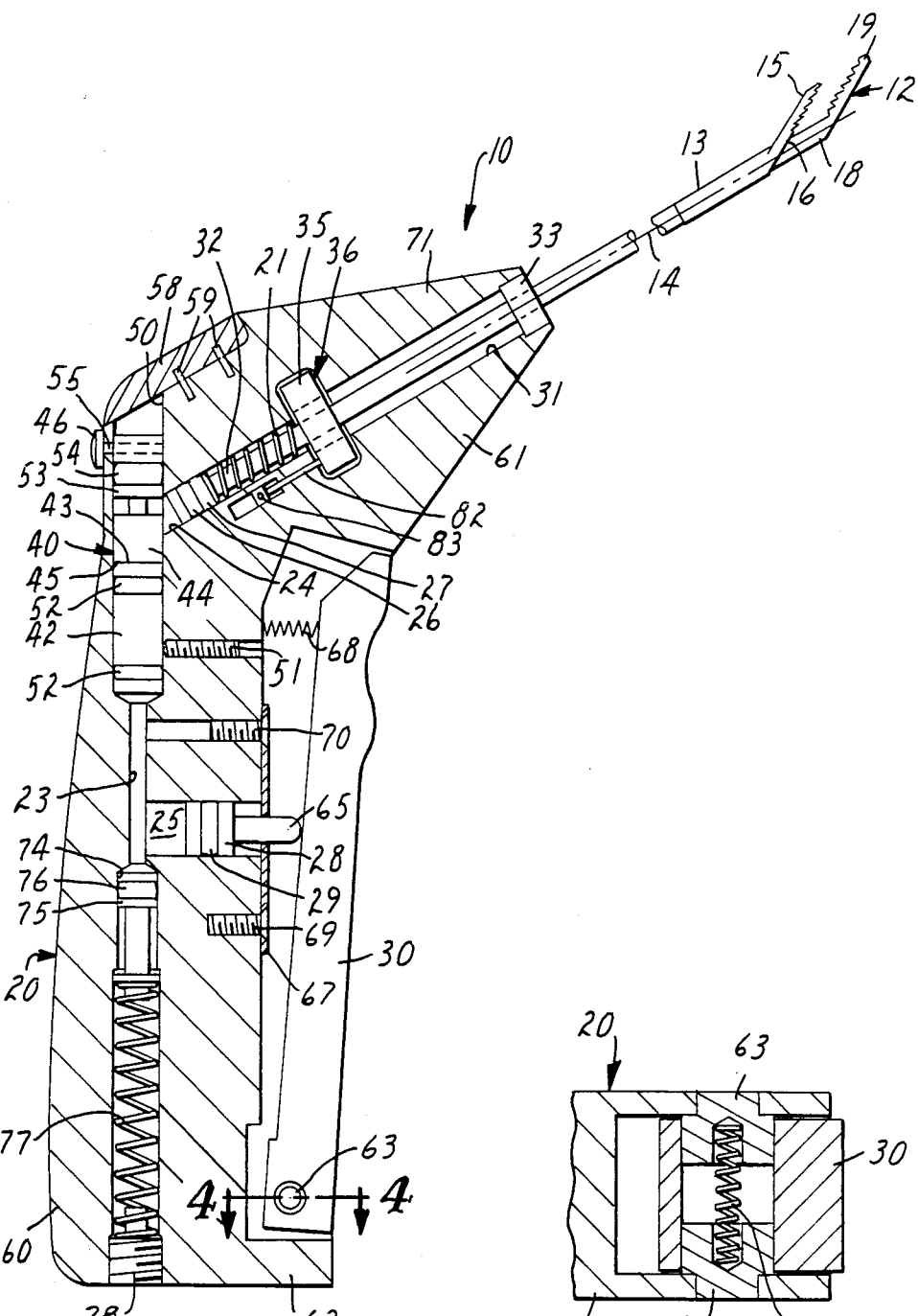
FIG. 2 is an enlarged sectional view of the instrument of FIG. 1.
Figure 4:
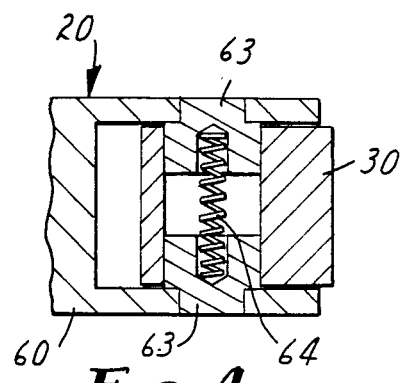
FIG. 4 is an enlarged sectional view taken approximately along line 4—4 of FIG. 2.

Referring now to the drawing there is shown a hydraulically operated surgical instrument according to the present invention generally designated by the reference numeral 10.

Generally the instrument 10 comprises a jaw assembly 12 including a hollow cylindrically tubular outer elongate member 13 having a central axis 14, and a first jaw member 15 fixed to and generally radially projecting from a first end 16 of the outer elongate member 13; and an inner elongate member 18 within and extending from the first end 16 of the outer elongate member 13 and having a second jaw member 19 fixed to and generally radially projecting from its end adjacent the first jaw member 15. Means are provided for mounting the jaw assembly 12 on a frame 20 of the instrument 10 with the first and second jaw members 15 and 19 in opposed generally parallel relationship while affording manual rotation of the jaw assembly 12 about the axis 14 relative to the frame 20; as are manually actuatable hydraulic means for moving the outer and inner elongate members 13 and 18 relative to each other from an open position with the jaw members 15 and 17 spaced from each other to a closed position with the jaw members 15 and 17 closely adjacent each other, and means in the form of a return spring 21 for biasing the jaw members 15 and 17 toward their open position to move the jaw members 15 and 16 from their closed position to their open position.

The manually actuatable hydraulic means for moving the outer and inner elongate members 13 and 18 includes (1) the frame 20 having a passageway 23 including first and second passageway portions 24 and 25; (2) a driven piston 27 having spaced flanges with an O-ring seal 26 therebetween sealably mounted in the first passageway portion 24 for movement along the first passageway portion 24 and fixed to the outer elongate member 13; (3) a drive piston 28 having spaced flanges with an O-ring seal 29 therebetween sealably mounted in the second passageway portion 25 for movement along the second passageway portion 25; (4) pressure transfer means comprising hydraulic fluid in the passageway 23 between the drive and driven pistons 28 and 27 for transferring pressure applied to the pressure transfer means by the drive piston 28 to the driven piston 27 to move the driven piston 27 along the first passageway portion 24 (and thereby the outer elongate member 13) in response to movement of the drive piston 28 along the second passageway portion 25; and (5) means including a trigger 30 adapted for manual activation to apply pressure to move the drive piston 28, and thereby the driven piston 27 and the first jaw member 15.

As illustrated, the means for mounting the jaw assembly 12 on the frame 20 with the first and second jaw members 15 and 17 in opposed relationship while affording manual rotation of the jaw assembly 12 about the axis 14 relative to the frame 20 comprises (1) the frame 20 having a socket 31 with portions of the outer and inner elongate members 13 and 18 adjacent a second nd° 32 of the outer elongate member 13 located within the socket 31; (2) bearing means between the portion of the outer elongate member 13 in the socket 31 and the frame 20 including a bearing 33 at an opening to the socket 31 and the second end 32 of the outer elongate member 13 fixed to the driven piston 27 for affording rotation of the jaw assembly 12 about the axis 14 relative to the frame 20; (3) a wheel 36 about the portion of the outer elongate member 13 in the socket 31, the wheel 36 being located in a through opening in the frame 20 which communicates with the socket 31 and having a knurled periphery projecting beyond the outer surface of the frame 20 where said periphery can be manually engaged to rotate the wheel 36; and (4) a pin 38 having its ends fixed in the wheel 36 and having a central portion extending radially through and fixed to the inner elongate member 18. The outer elongate member 13 has axially extending slots 39 through which the pin 38 extends, which slots 39 afford axial movement of the outer elongate member 13 relative to the inner elongate member 18 between the open and closed positions of the jaw members 15 and 17, and the slots 39 are defined by side walls in engagement with the pin 38 so that the outer elongate member 13 will be rotated with the inner elongate member 18 upon manual rotation of the wheel 36 relative to the frame 20.

As illustrated, the wheel 36 comprises an inner portion 34 in which the ends of the pin 38 are fixed and which can move through the socket 31 to facilitate assembling the instrument 10, and an outer ring-like portion 35 having the knurling on its outer surface which is secured to the inner portion 34 by set screws 37.

The manually actuatable hydraulic means for moving the outer and inner elongate members 13 and 18 includes manually actuatable means in the form of a check valve assembly 40 for preventing movement of the jaw members 15 and 17 from their closed position toward their open position under the influence of the return spring 21 and pressure being applied between the jaw members 15 and 17, and for affording actuation of the manually actuatable hydraulic means to move the jaw members 15 and 17 from their open position toward their closed position when the means for preventing movement is actuated.

The check valve assembly 40 comprises (1) a plug 42 having a circular sealing surface 43 oriented transverse of the passageway 23 and adjacent the driven piston 27 and having a through opening 41 defining a portion of the passageway 23 opening through only a portion of the sealing surface 43 adjacent on side thereof; (2) a valve 44 having a circular valve surface 45 adjacent and adapted for sealing engagement with the sealing surface 43, the valve 44 being a cup-like member, being axially movable in the passageway 22, and having a through opening 48 defining a portion of the passageway 23 opening through only a portion of the valve surface 45 adjacent one edge thereof; (3) manually activatable means activatable by moving a button 46 to rotate the valve 44 for affording rotational movement of the valve 44 between a release position with the openings 41 and 48 in the sealing surface 43 and the valve surface 45 in alignment and a seal position with the openings 41 and 48 in the sealing surface 43 and the valve surface 45 out of alignment; and (4) means in the form of a spring 47 for biasing the valve 44 toward the plug 42 to bias the valve and sealing surfaces 45 and 43 into sealing engagement when the valve 44 is rotated to its seal position to prevent movement of hydraulic fluid toward the drive piston 28 while affording movement of hydraulic fluid toward the driven piston 27 through the plug 42 and the valve 44 by separation of the valve surface 45 from the sealing surface 43 in opposition to the spring 47.

The plug 42 and valve 44 are located in a cylindrical bore 50 in the frame 20, with the plug 42 being held therein by a set screw 51 and having O-ring seals 52 about its periphery to be sure hydraulic fluid will flow only through the through opening 41.

The manually activatable means for rotating the valve 44 includes an actuating member 53 also located in the bore 50 which has an O-ring seal 54 around its periphery to maintain hydraulic fluid in the passageway 23. The actuating member 53 is attached to the button 46 by a pin 55 extending through a slot in the frame 20 that affords rotation of the actuating member 53 about its axis between release and hold positions by movement of the button 46, and includes a transverse pin 56 with projecting ends engaged in axially extending slots 57 in the valve 44 so that such movement of the button 46 will cause corresponding rotation of the valve 44 between its release and seal positions. The axially extending slots 57 in the cup 44 allow the valve 44 to move axially in the bore 50 to allow hydraulic fluid to flow toward the driven piston 27 through the plug 42 and valve 44 by separation of the valve surface 45 from the sealing surface 43 in opposition to the spring 47 when the valve 44 is in its seal position. The end of the spring 47 opposite the valve 44 is supported in a recess in the actuating member 53. A cap-like part 58 of the frame 20 held in place by a pair of screws 59 closes the outer end of the bore 50.

The frame 20 comprises a first or handle portion 60 which is elongate in a first direction and has first and second ends 61 and 62, which handle portion 60 is adapted for manual engagement. The second passageway portion 25 is disposed generally centrally along the handle portion 60 within its central axis generally at a right angle to the first direction. The means adapted for manual activation to apply pressure to move the drive piston 28 comprises the trigger 30 which has one end pivotably attached to the frame 20 at the second end 62 of the handle portion 60 by opposed shoulder pins 63 biased outwardly by a retaining spring 64, has a central part overlying the end of the drive piston 28 opposite the pressure transfer means in the passageway 23, and is biased away from the frame 20 by a spring 68. Means in the form of a projection 65 from the drive piston 28 (which projection 65 projects through a plate 67 fixed to the frame 20 by screws 69 and 70 that retains the drive piston 28 in the second passageway portion 25) is in engagement between the trigger 30 and the drive piston 28 to move the drive piston 28 along the first passageway 23 portion toward the pressure transfer means when the trigger 30 is manually moved toward the handle portion 60. The frame 20 further includes a second or projecting portion 71 at the first end 61 of the handle portion 60. The socket 31 in which the portions of the outer and inner elongate members 13 and 18 are located is positioned in the projecting portion 71 with the central axis 14 of the outer elongate member 13 disposed at about a 60 degree included angle with respect to the first direction the opening of the socket 31 from which the elongate members 13 and 18 project is located on the side of the frame 20 on which the trigger 30 is mounted, the knurled periphery of the wheel 36 projects from opposite side surfaces of the projecting portion 71 flanking the trigger 30, and the button 46 for affording movement of the valve 44 between the release and sealing positions is located adjacent the juncture between the handle and projecting portions 60 and 71 on the side of the handle portion 60 opposite the trigger 30.

The manually actuatable hydraulic means for causing relative movement between the outer and inner elongate members 13 and 18 in the hydraulically operated surgical instrument 10 includes means for limiting the force that can be applied between the jaw members 15 and 17 when the jaw members 15 and 17 are moved toward their closed position. The frame 20 has a third passageway portion 74 intersecting a portion of the passageway 23 between the first and second passageway portions 24 and 25. A relief piston 75 comprising spaced flanges with an O-ring seal 76 therebetween is sealably mounted in the third passageway portion 74 for movement along the third passageway portion 75 between a normal position and relief positions expanding the volume of the passageway 23 containing the hydraulic fluid; and means in the form of a relief coil spring 77 are provided for biasing the relief piston 75 toward its normal position with a predetermined force. The end of the relief coil spring 77 opposite the relief piston 75 is supported by a screw plug 78 threadably engaged with the frame 20 that can be removed to afford removal of the relief spring 77 and relief piston 75 and filling the passageway 23 with hydraulic fluid.

Means are also provided for releasably locking the wheel 36 and thereby the projecting jaw members 15 and 19 at a predetermined orientation with respect to the frame 20. The wheel 36 has a ring of axially extending sockets 80 opening from its side adjacent the handle portion 60 of the frame 20. A lock pin 82 is slidably mounted in a passageway in the frame 20 for movement between engaged and disengaged positions with respect to one of the sockets 80 aligned with it, and the lock pin 82 is attached by a transverse attaching pin 83 to a pair of actuators 84, one on each side of the projecting portion 61 of the frame 20, which actuators 84 are adapted for manual engagement to move the lock pin 82 between its engaged and disengaged positions.

To operate the instrument 10, a user simply positions the jaw members 15 and 19 on opposite sides of an object such as tissue to be engaged and squeezes on the trigger 30 to close the jaw members 15 and 19 on the object. Such closing is accomplished by movement of the drive piston 28 caused by movement of the trigger 30 and corresponding movement of the driven piston 27 because of the hydraulic fluid in the passageway 23, which driven piston 27 in turn moves the outer elongate member 13 relative to the inner elongate member 18 to close the jaw members 15 and 19. If the user desires to change the orientation of the jaw members 15 and 19 with respect to the handle frame portion 60 he is grasping to actuate the trigger 30, he can easily do so (assuming the lock pin 82 is in its release position) by manually engaging and rotating one of the portions of the wheel 36 projecting from the sides of the frame 20, after which the user can, if desired, lock the wheel 36 in that new position by moving one of the actuators 84 to engage the lock pin 82 with an aligned one of the ring of sockets 80 in the wheel 36. If the user wishes to have the jaw members 15 and 19 close and open in response his depressing and releasing of the trigger 30, he sets the button 46 adjacent his thumb to its release position so that the valve 44 moves to its release position at which the openings 41 and 48 through the sealing and valve surfaces 43 and 45 are in alignment and the hydraulic fluid can flow freely in both directions through the check valve assembly 40. If, instead, the user wishes to have the jaw members 15 and 19 remain closed after he has depressed the trigger 30, he moves the button 46 to its hold position and thereby the valve 44 to its seal position at which the openings 41 and 48 through the sealing and valve surfaces 43 and 45 are out of alignment. If this is done after the user depresses the trigger 30, the jaw members 15 and 19 will retain all of the applied clamping force between the jaws 15 and 19 because of the rotary motion of the valve 44 to cause sealing engagement of the valve and sealing surfaces 45 and 43 that causes no displacement of hydraulic fluid between the plug 42 and driven piston 27. The button 46 can also be moved to its seal position before the trigger 30 is depressed whereupon the hydraulic fluid can flow past the check valve assembly 40 toward the driven piston 27 by lifting the valve 44 against the spring 47, but hydraulic fluid can not flow past the check valve assembly 40 toward the drive piston 28 because of the sealing engagement of the valve and sealing surfaces 45 and 43. If the user later wishes to release the object, this is easily done by moving the button 46 to its release position. The force that can be applied between the jaw members 15 and 19 is limited by the relief piston 75 which will move in the third passageway portion 74 against the bias of the relief spring 77 when the predetermined maximum force between the jaw members 15 and 19 is reached, after which movement of the jaw members 15 and 19 will stop and the predetermined force will be maintained.

The present invention has now been described with reference to one embodiment thereof. It will be apparent to those skilled in the art that many changes can be made in the embodiment described without departing from the scope of the present invention. For example, the first and second jaw members 15 and 19 could have many other shapes intended for special purposes, such as (but not limited to) those shapes illustrated in U.S. Pat. No. 3,752,161. Also, it may be desirable to form the portion the plug 42 or valve defining the sealing or valve surface 43 or 45 of a slightly compressible material to help accommodate expansion of the hydraulic fluid in the first passageway portion 24 if the instrument is heated such as by an autoclave when the valve is in its seal position so that the openings 41 and 48 through the sealing and and valve surfaces 43 and 45 are out of alignment. Thus the scope of the present invention should not be limited to the structures described in this application, but only by structures described by the language of the claims and the equivalents of those structures.

We claim:

1. A hydraulically operated surgical instrument comprising:
    a frame;
    a jaw assembly including an hollow tubular outer elongate member having a central axis, first and second opposite ends, and a first jaw member fixed to and generally radially projecting from said first end; and
    an inner elongate member within and extending from the first end of said outer elongate member and having a second jaw member fixed to and generally radially projecting from its end adjacent said first jaw member;
    means for mounting said jaw assembly on said frame with said first and second jaw members in opposed relationship while affording manual rotation of said jaw assembly about said axis relative to said frame; and
    manually actuatable hydraulic means for causing relative movement between said outer and inner elongate members between an open position with said jaw members spaced from each other, and a closed position with said jaw members closely adjacent each other including reusable force-limiting means for preventing hydraulic pressure from exceeding a predetermined pressure to limit the force that can be applied between said jaw members when said jaw members are moved toward said closed position by manual activation of said hydraulic means, the reusable force-limiting means comprising a spring-biased pressure relief piston closing a portion of the hydraulic means, and movable at the predetermined hydraulic pressure against the spring-bias from a normal position to a relief position for relieving hydraulic pressure to limit the force applied between the jaw members.

2. A hydraulically operated surgical instrument according to claim 1 wherein said means for mounting said jaw assembly on said frame with said first and second jaw members in opposed relationship while affording manual rotation of said jaw assembly about said axis relative to said frame comprises:
    said frame having a socket with portions of said outer and inner elongate members adjacent the second end of said outer member located within said socket;
    bearing means between the portion of said outer elongate member in said socket and said frame for affording rotation of said jaw assembly about said axis relative to said frame;
    a wheel about the portion of said outer hollow tubular member in said socket, said frame having a through opening intersecting said socket in which opening said wheel is positioned, and said wheel having a periphery having portions projections from said opening beyond the outer surface of said frame; and
    a pin having its ends fixed in said wheel and having a central portion extending radially through and fixed to said inner elongate member;
    said outer hollow tubular elongate member having axially extending slots through which said pin extends affording axial movement of said outer elongate member relative to said inner elongate member between said open and closed positions, and said slots being defined by side walls in engagement with said pin so that said outer elongate member will be rotated with said inner elongate member upon manual rotation of said wheel relative to said frame.

3. A hydraulically operated surgical instrument according to claim 2 further including manually actuatable means for releasably locking said wheel against rotation at a predetermined position relative to said frame.

4. A hydraulically operated surgical instrument according to claim 3 wherein said means for releasably locking is provided by said wheel having a circular array of axially extending sockets, and said instrument further including a locking pun mounted on said frame for movement between a release position spaced from said wheel, and an engage position engaged in one of said sockets in said wheel.

5. A hydraulically operated surgical instrument according to claim 1 wherein said manually actuatable hydraulic means for causing relative movement between said outer and inner elongate members includes manually actuatable means for preventing movement of said jaw members from said closed position toward said open position.

6. A hydraulically operated surgical instrument according to claim 5 wherein said manually actuatable means for preventing movement of said jaw members from said closed position toward said open position includes one way valve means for affording actuation of said manually actuatable hydraulic means to move said jaw members from said open position toward said closed position when said means for preventing movement is actuated.

7. A hydraulically operated surgical instrument according to claim 1 wherein the reusable force-limiting means provides means for maintaining force between the jaw members to prevent movement of the jaw members when the limiting force is reached until the manually actuatable hydraulic means is manually deactivated.

8. A hydraulically operated surgical instrument comprising:
   a frame;
   a jaw assembly including an hollow tubular outer elongate member having a central axis, first and second opposite ends, and a first jaw member fixed to and generally radially projecting from said first end; and
   an inner elongate member within and extending from the first end of said outer elongate member and having a second jaw member fixed to and generally radially projecting from its end adjacent said first jaw member;
   means for mounting said jaw assembly on said frame with said first and second jaw members in opposed relationship while affording manual rotation of said jaw assembly about said axis relative to said frame; and
   manually actuatable hydraulic means for causing relative movement between said outer and inner elongate members between an open position with said jaw members spaced from each other, and a closed position with said jaw members closely adjacent each other including means for limiting the force that can be applied between said jaw members when said jaw members are moved toward said closed position by manual activation of said hydraulic means;
   said manually actuatable hydraulic means for causing relative movement between said outer and inner elongate members including:
   said frame having a passageway including first and second passageway portions;
   a driven piston sealably mounted in said first passageway portion for movement along said first passageway portion and coupled to one of said elongate members;
   a drive piston sealably mounted in said second passageway portion for movement along said second passageway portion;
   pressure transfer means comprising hydraulic fluid in said passageway between said drive and driven pistons for transferring pressure applied to said pressure transfer means by said drive piston to said driven piston to move said driven piston along said first passageway portion in response to movement of said drive piston along said second passageway portion; and
   means adapted for manual activation to apply pressure to move said drive piston; and
   manually actuatable means for preventing movement of said jaw members from said closed position toward said open position, said manually actuatable means for preventing movement of said jaw members from said closed position toward said open position including one way valve means for affording actuation of said manually actuatable hydraulic means to move said jaw members from said open position toward said closed position when said means for preventing movement is actuated;
   said manually actuatable means for preventing movement of said jaw members from said closed position toward said open position and said means for affording actuation of said manually actuatable hydraulic means to move said jaw members from said open position toward said closed position when said means for preventing movement is actuated comprising:
   a check valve assembly defining a portion of said passageway between said first and second passageway portions comprising:
   a plug having a sealing surface transverse of said passageway and adjacent said driven plunger and having a through opening defining a portion of said passageway opening through only a portion of said sealing surface;
   a valve having a valve surface adjacent and adapted for sealing engagement with said sealing surface, said valve having a through opening defining a portion of said passageway opening through only a portion of said valve surface;
   manually activatable means for affording movement of said valve between a release position with said openings in said sealing surface and said valve surface in alignment and a seal position with said openings in said sealing surface and said valve surface out o alignment; and
   means for biasing said valve toward said plug to bias said valve and sealing surfaces into sealing engagement when said valve is moved to its release position to prevent movement of hydraulic fluid toward said drive piston while affording movement of hydraulic fluid toward said driven piston through said plug and said valve by separation of said valve surface from said sealing surface in opposition to said means for biasing.

9. A hydraulically operated surgical instrument comprising:
   a frame;
   a jaw assembly including an hollow tubular outer elongate member having a central axis, first and second opposite ends, and a first jaw member fixed to and generally radially projecting from said first end; and
   an inner elongate member within and extending from the first end of said outer elongate member and having a second jaw member fixed to and generally radially projecting from its end adjacent said first jaw member;
   means for mounting said jaw assembly on said frame with said first and second jaw members in opposed relationship while affording manual rotation of said jaw assembly about said axis relative to said frame; and
   manually actuatable hydraulic means for causing relative movement between said outer and inner elongate members between an open position with said jaw members spaced from each other, and a closed position with said jaw members closely adjacent each other including means for limiting the force that can be applied between said jaw members when said jaw members are moved toward said closed position by manual activation of said hydraulic means;
   said means for mounting said jaw assembly on said frame with said first and second jaw members in opposed relationship while affording manual rotation of said jaw assembly about said axis relative to said frame comprising:
   said frame having a socket with portions of said outer and inner elongate members adjacent the second end of said outer member located within said socket;

bearing means between the portion of said outer elongate member in said socket and said frame for affording rotation if said jaw assembly about said axis relative to said frame;

a wheel about the portion of said outer hollow tubular member in said socket, said frame having a through opening intersecting said socket in which opening said wheel is positioned, and said wheel having a periphery having portions projecting from said opening beyond the outer surface of said frame; and a pin having its ends fixed in said wheel and having a central portion extending radially through and fixed to said inner elongate member;

said outer hollow tubular elongate member having axially extending slots through which said pin extends affording axial movement of said outer elongate member relative to said inner elongate member between said open and closed positions, and said slots being defined by side walls in engagement with said pin so that said outer elongate member will be rotated with said inner elongate member upon manual rotation of said wheel relative to said frame;

said manually actuatable hydraulic means for causing relative movement between said outer and inner elongate members including:

said frame having a passageway including first and second passageway portions;

a driven piston assembly sealably mounted in said first passageway portion for movement along said first passageway portion and coupled to one of said tubular members;

a drive piston sealably mounted in said second passageway portion for movement along said second passageway portion;

pressure transfer means comprising hydraulic fluid in said passageway between said drive and driven pistons for transferring pressure applied to said pressure transfer means by said drive piston to said driven piston to move said driven piston along said first passageway portion in response to movement of said drive piston along said second passageway portion; and means adapted for manual activation to apply pressure to move said drive piston; and said instrument further including manually actuatable means for preventing movement of said jaw members from said closed position toward said open position and means for affording actuation of said manually actuatable hydraulic means to move said jaw members from said open position toward said closed position when said means for preventing movement is actuated comprising:

a check valve assembly defining a portion of said passageway between said first and second passageway portions comprising:

a plug having a sealing surface transverse of said passageway and adjacent said driven piston and having a through opening defining a portion of said passageway opening through only a portion of said sealing surface;

a valve having a valve surface adjacent and adapted for sealing engagement with said sealing surface, said valve having a through opening defining a portion of said passageway opening through only a portion of said valve surface;

manually activatable means for affording rotary movement of said valve between a release position with said openings in said sealing surface and said valve surface in alignment and a seal position with said openings in said sealing surface and said valve surface out of alignment; and means for biasing said valve toward said plug to bias said valve and sealing surfaces into sealing engagement when said valve is rotated to its release position to prevent movement of hydraulic fluid toward said drive piston while affording movement of hydraulic fluid toward said driven piston through said plug and said valve by separation of said valve surface from said sealing surface in opposition to said means for biasing.

10. A hydraulically operated surgical instrument according to claim 9 wherein:

said frame comprises a handle portion elongate in a first direction, having first and second ends, and adapted from manual engagement;

said second passageway portion is disposed generally centrally along said handle portion with its central axis generally at a right angle to said first direction;

said means adapted for manual activation to apply pressure to move said drive piston comprises:

a trigger having one end pivotably attached at one end of said handle portion and having a part overlying the end of said drive piston opposite said pressure transfer means; and means in engagement between said trigger and said drive piston to move said drive piston along said first passageway portion toward said pressure transfer means when said trigger is moved toward said handle portion; and said frame further includes a projecting portion at the first end of said handle portion, said projecting portion having said socket in which said portions of said outer and inner elongate members are located with the central axis of said outer elongate member disposed at about a 60 degree included angle with respect to said first direction, the opening of said socket from which said elongate members project being on the side of said frame on which said trigger is mounted, and said periphery of said wheel projecting from opposite side surfaces of said projecting frame portion flanking said trigger; and said manually activatable means for affording movement of said valve between said release and sealing positions is located adjacent the juncture between said handle and projecting portions on the side of said handle portion opposite said trigger.

* * * * *

UNITED STATES PATENT AND TRADEMARK OFFICE
CERTIFICATE OF CORRECTION

PATENT NO. : 4,848,338

DATED : July 18, 1989

INVENTOR(S) : De Satnick et al.

It is certified that error appears in the above-identified patent and that said Letters Patent is hereby corrected as shown below:

Title Page, Item [57]:
Abstract, line 5, "elongated" should read --elongate--.

Col. 2, line 47, after "operated" insert --surgical--.

Col. 3, line 48, "nd" should read --end--.

Col. 8, line 46, "pun" should read --pin--.

Col. 10, line 23, "o" should read --of--.

Col. 11, line 5, "if" should read --of--.

Signed and Sealed this

Thirtieth Day of October, 1990

Attest:

HARRY F. MANBECK, JR.

Attesting Officer

Commissioner of Patents and Trademarks